US007895055B2

(12) United States Patent
Schneider et al.

(10) Patent No.: US 7,895,055 B2
(45) Date of Patent: Feb. 22, 2011

(54) METHOD AND SYSTEM TO OPTIMIZE AND AUTOMATE CLINICAL WORKFLOW

(75) Inventors: Henning Schneider, Erlangen (DE); Sultan Haider, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1228 days.

(21) Appl. No.: 11/300,547

(22) Filed: Dec. 14, 2005

(65) Prior Publication Data

US 2007/0136089 A1 Jun. 14, 2007

(51) Int. Cl.
*G06Q 10/00* (2006.01)
*G06Q 50/00* (2006.01)

(52) U.S. Cl. .............................................. 705/2; 705/3

(58) Field of Classification Search .................. 703/2–3
See application file for complete search history.

(56) References Cited

U.S. PATENT DOCUMENTS

2002/0183979 A1* 12/2002 Wildman .................... 702/188
2003/0074222 A1* 4/2003 Rosow et al. .................. 705/2
2003/0225316 A1* 12/2003 Abraham-Fuchs et al. .. 600/300

OTHER PUBLICATIONS

Soarian Clinical Access of Siemens—Printout.
Activity Analysis and Workflow Automation in Clinical Procedures.

* cited by examiner

*Primary Examiner*—Gerald J. O'Connor
*Assistant Examiner*—Minnah Seoh
(74) *Attorney, Agent, or Firm*—Schiff Hardin LLP

(57) ABSTRACT

In a method for optimizing and automating patient clinical workflow where medical personnel oversee a patient from intake to an end of the clinical workflow, at least one patient monitoring unit is provided which monitors clinical activities related to the patient during at least a portion of the clinical workflow. A centralized communication platform is provided which is controlled by, and which provides information output to, at least one of the medical personnel. The communication platform receives different types of information including at least patient monitoring unit information, rules information, structured information, and IT information. With the communication platform, the different information types are processed and management outputs are provided to the at least one medical personnel for decision making and overall management of the clinical workflow.

17 Claims, 3 Drawing Sheets

METHOD AND SYSTEM TO OPTIMIZE AND AUTOMATE CLINICAL WORKFLOW

BACKGROUND

Clinical workflows, meaning a chain of events and process steps from a first contact of a patient until his release out of a care program, is a complex cooperation of doctors, clinical staff, diagnostic questions, experimentations done by different departments, modalities, clinical data and conclusions. Such a clinical workflow is shown at 10 with steps 10 A-G (See FIG. 1). Due to a fast medical evolution of the last few years, these workflows have been expanded and adapted to new methods, techniques, systems and modalities without paying attention to integrating these changes into one aligned workflow.

Today, clinical workflows comprise a huge amount of different data, information, interfaces, options and parameters which have to be attended or entered by the doctors and clinical staff (See rules 12A-12F, information exchange 13A-13G, and Information Technology (IT) information 11A-11F in FIG. 1). Some of the same data has to be entered several times into different systems and modalities. For example, Cathlabs have been examined where key patient data (record number, name, age and weight) has to be entered manually in four different systems during one medical examination. Each of these manual data entries and unstructured presentations of information can be an additional source of error which causes additional costs and possibly dangerous complications.

During the last few years pressure to measure and optimize clinical workflows has increased enormously. Hospitals have to prove their quality and therefore have to provide a lot of additional data like timestamps, duration, and cost of process steps. This causes additional demands in an isolated fashion to the clinical staff 14 and the IT systems 11 and again increases the amount of data to deal with.

As to most parts of this problem doctors and clinical staff 14 have been left alone.

One attempt to decrease complications and entry of wrong data is a well organized and documented workflow. This is done most of the time by paper checklists such as in emergency departments.

For some other clinical departments there are special IT systems developed like Radiology Information Systems 11B (RIS) which solve some departmental lack of integration, but still require a lot of manual data entries.

There are a few modern IT systems such as SOARIAN 11E which now supports a main clinical workflow and can structure information depending on the user and situation. These systems can guide the overall workflow on a general level by a "workflow engine," but do not support the departmental processes, which are the most critical ones. The different prior art IT systems are shown at 11 in FIG. 1: Hospital Information System 11A (HIS); Radiology Information System 11B (RIS); Cardiac Information System 11C (CIS); Picture Archiving System 11D (PACS) (which is, for example, images where results of modalities are stored); Specialized Information System 11 (SOARIAN) of Siemens AG, Munich, Germany (a workflow based system); and other IT systems 11F.

In summary, the prior art systems can either support single process steps or very general high level workflow only and are dependent on manual data entries. Without these entries, or with wrong entries, these systems are blind or cause problems and complications.

SUMMARY

In a method for optimizing and automating patient clinical workflow where medical personnel oversee a patient from intake to an end of the clinical workflow, at least one patient monitoring unit is provided which monitors clinical activities related to the patient during at least a portion of the clinical workflow. A centralized communication platform is provided which is controlled by, and which provides information output to, at least one of the medical personnel. The communication platform receives different types of information including at least patient monitoring unit information, rules information, structured information, and IT information. With the communication platform, the different information types are processed and management outputs are provided to the at least one medical personnel for decision making and overall management of the clinical workflow.

DESCRIPTION OF THE PREFERRED EMBODIMENT

Figure 1:
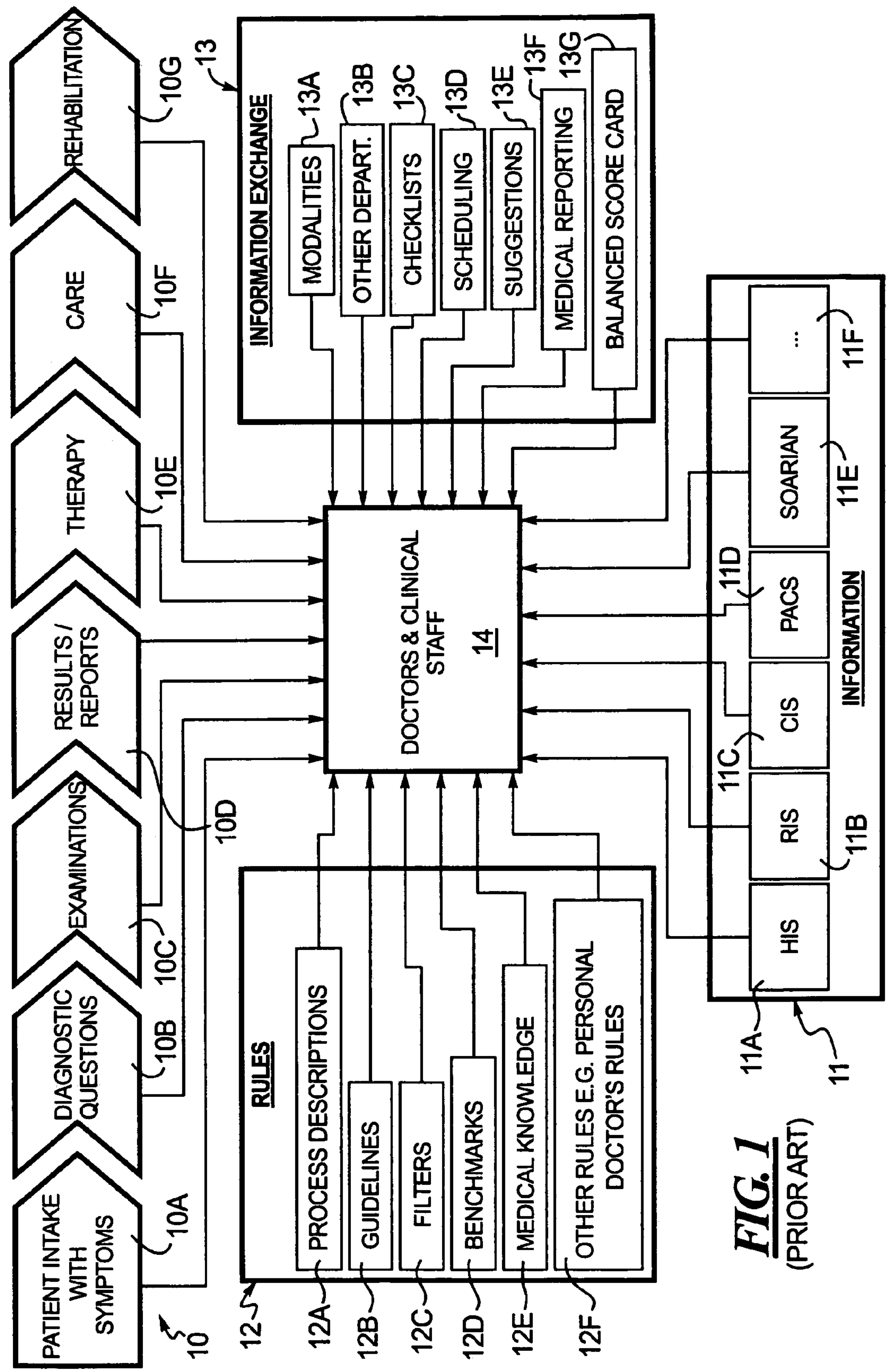
FIG. 1 is a diagram illustrating the prior art clinical workflow steps individually and personally administered by doctors and/or clinical staff using IT systems, rules, and information exchange.

For the purposes of promoting an understanding of the principles of the invention, reference will now be made to the preferred embodiment illustrated in the drawings and specific language will be used to describe the same. It will nevertheless be understood that no limitation of the scope of the invention is thereby intended, such alterations and further modifications in the illustrated device, and/or method, and such further applications of the principles of the invention as illustrated therein being contemplated as would normally occur now or in the future to one skilled in the art to which the invention relates.

Figure 2:
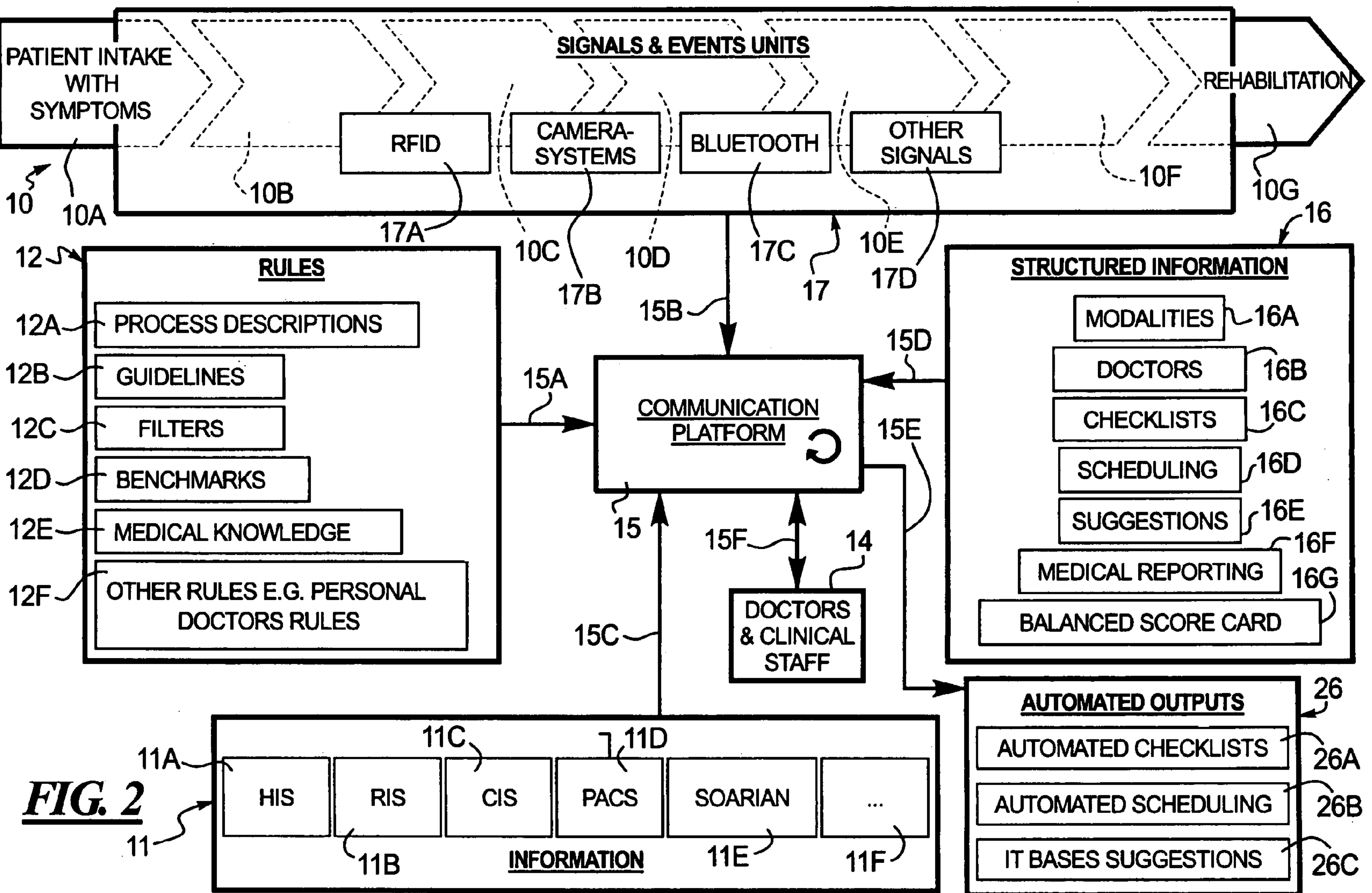
FIG. 2 is a diagram of the preferred embodiment showing a communication platform having a server receiving signal and event unit information concerning the patient from beginning to end of the clinical workflow, rule information, structured information, and IT information, and wherein doctors and clinical staff receive output information and have a high level interaction with the communication platform.

The preferred embodiment provides, as shown in FIG. 2 a complete integrated link between automated data entries and a situation and workflow based information and communication system (communication platform 15), and which automatically recognizes the situation and supports and guides the doctors/clinical staff 14 through the workflow 10.

Figure 3:
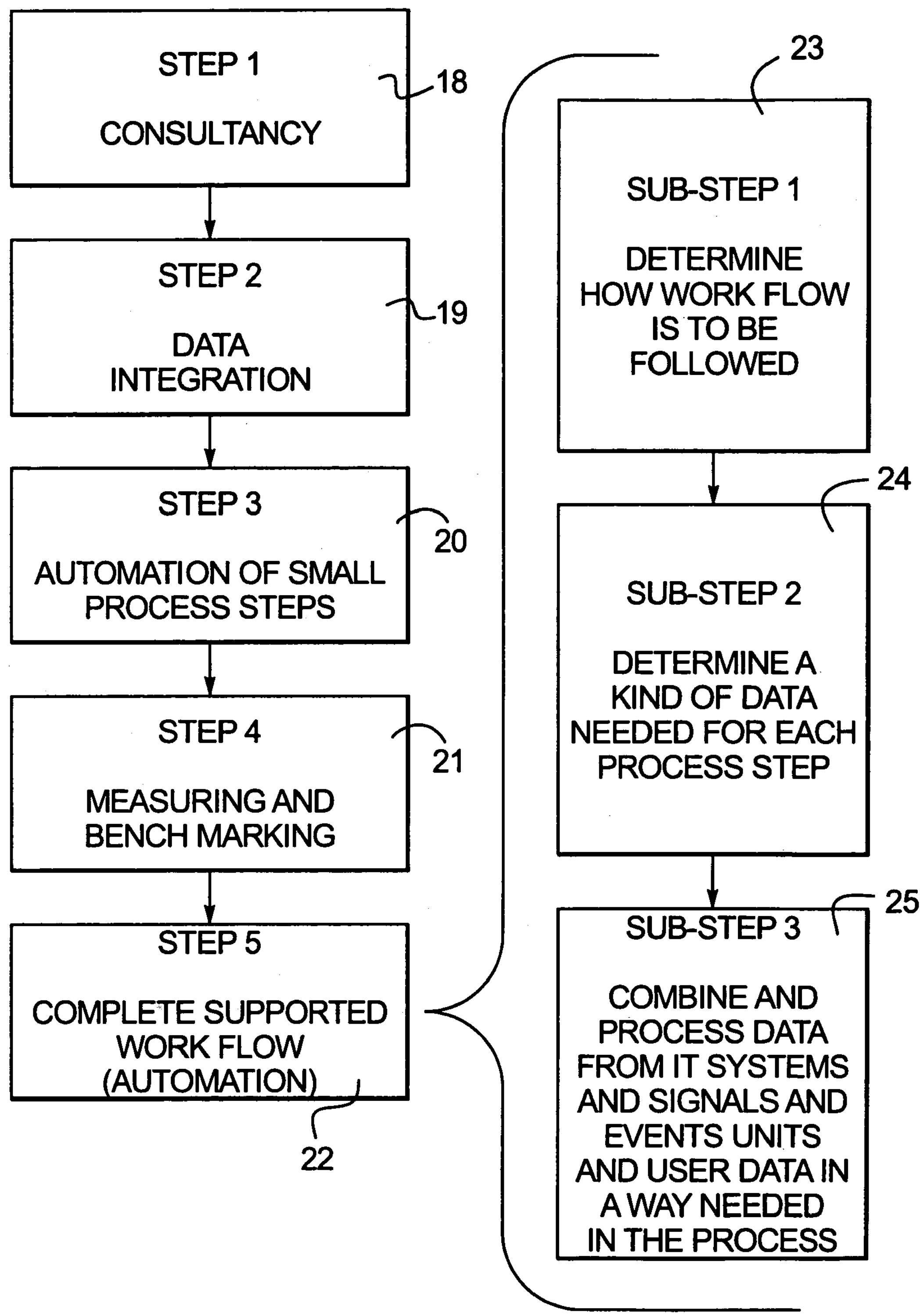
FIG. 3 shows method steps for optimizing and automating clinical workflow.

As shown in FIG. 3, the software in the communication platform of the system and method of the preferred embodiment comprises the following five steps described hereafter: 1) consultancy 18; 2) data integration 19; 3) automation of small process steps 20; 4) measuring and benchmarking 21; and 5) complete supported workflow (automation) 22.

For consultancy (step 1), first the system and method documents and analyzes the actual clinical workflow 10 with all parameters and components (duration, cost, interfaces, organization, complications, problems etc.) This provides the description and definition of: low hanging fruits (easy changes with high performance); process steps & checklists; modalities; guidelines & rules; organization; and benchmarks. This will lead to improvement of: process steps; utilization of modalities; organization; and architectural layout.

For the system integration (step 2), the IT landscape and information flow are analyzed and documented. Systems are checked for interfaces and redundant data.

This will give the description and definition of: information flow; interfaces; IT-systems; information lags; redundant data; and information requirements. This will lead to the improvement of: information interfaces; redundancy of data; information flow; and IT-Systems.

For automation of small process steps (step 3), the goal is the decrease in manual data entries and to directly reduce medical errors in the clinical routines. Technical solutions which are used, called signals and events units at 17 in FIG. 2, are: RFID unit 17A; camera systems 17B such as video inputs from the modalities (e.g. Magnetic Resonance (MR), Computed Tomography (CT), Nuclear Medicine (NM)) where localizer images can be used for registering patient positioning/weight; BLUETOOTH equipment communication signals 17; and other signals 17D such as smart cards carrying patient data etc.

The above-described step 4 comprises measuring the use of system components. With tools like Computer Tomography (CT), and Magnetic Resonance (MR), system utilization may be used. It gives control of improvement and the way the process/workflow should be followed and works as a baseline for the decision matrix. This will give description and definition of: quality measures; benchmarks; balanced score card; and utilization management. This will lead to improvement of: quality management; workflow management; and management "cockpit view".

For the complete supported workflow (automation) (step 5), all the components are combined in, or send data to, one IT system, the communication platform 15. As shown by the sub-steps for step 5 in FIG. 3, in a first sub-step 23 the system determines how the workflow is to be followed by a decision matrix based on general workflow knowledge, medical guideline and personal experience of the medical professional. In a second sub-step 24 the system automatically determines a kind of data needed for each process step. The system 15 comprises a self learning and training algorithm based on artificial neural networks, genetic algorithm etc. As a third sub-step 25 the system takes the data from the different medical IT systems 11, signals and events units 17 such as RFID 17A and camera systems 17B etc. The system 15, (communication platform) combines and processes the data from the different systems and uses it in the way it is needed in the process. It is not another database for clinical data. This provides automated outputs 26 which are a description and definition of structured information 16 and which includes: automated checklists 26A; automated scheduling 26B; and automated IT bases suggestions 26C. All of these outputs are available to the doctors and clinical staff 14. This results in an improvement of: process flow; process quality; and workflow management.

The system of the preferred embodiment shown in FIG. 2 employs as the heart of the system the communication platform 15. This communication platform 15 processes the rules data 12 from particular types of rules information 12A-F input at 15A. It also processes structured information 16 such as 16A-16G at input 15D. It also receives patient signals and events information 17 on input 15B, such as from signals and events units 17A-17D. These signals and events units provide information as the patient progresses through the clinical workflow shown at 10 from the beginning such as the intake of the patient with symptoms at 10A, through the completion of the clinical workflow where the patient receives rehabilitation at 10G. For example, the patient may carry an RFID tag which is picked up by the RFID unit 17A. The camera systems unit 17B, may for example, observe the patient in various clinical situations or undergoing various modalities such as MR. Cameras, for example, may observe the patient as he undergoes the MR procedure, such cameras checking on proper MR procedures and checking on the patient as he undergoes the MR procedures. BLUETOOTH equipment communication units 17C provide for communication between various types of equipment at various steps of the clinical workflow.

The doctors and clinical staff 14 have the final decision making authority and their communication with the communication platform 15C is at a high level, thus minimizing the decision making of the doctors and clinical staff to the high level decisions.

The communication platform 15 also receives information from the IT systems 11 such as hospital information systems 11A, radiology information systems 11B, cardiology information systems 11C etc.

The communication platform 15 outputs on line 15E automated management information outputs for doctors and clinical staff 14 (medical staff) including automated check lists 26A, automatic scheduling 26B, and IT bases suggestions 26C.

While a preferred embodiment has been illustrated and described in detail in the drawings and foregoing description, the same is to be considered as illustrative and not restrictive in character, it being understood that only the preferred embodiment has been shown and described and that all changes and modifications that come within the spirit of the invention both now or in the future are desired to be protected.

We claim as our invention:

1. A method for automating and optimizing patient clinical workflow wherein medical personnel oversee a patient from intake through care in the clinical workflow, comprising the steps of:

providing said clinical workflow comprising at least the following steps obtaining patient information including symptoms information as workflow information, obtaining patient diagnostics response information from the patient to diagnostic questions to said patient as further workflow information, obtaining patient examination information for said patient as further workflow information, acquiring result/report information for said patient as further workflow information, providing patient therapy, providing patient care, and providing patient rehabilitation, said workflow and further workflow information being obtained in advance of the patient's treatment for use in automatically determining for said patient an optimized workflow to be followed for said patient;

providing a patient monitoring unit in the form of a radio frequency identification tag providing tracking location information of the patient during said clinical workflow;

providing at least one equipment communication unit for providing operation information for equipment used in the workflow in examining, treating, or caring for the patient;

providing at least one information technology system providing information technology medical information for said patient as said workflow information;

providing rules information as said workflow information;

providing medical personnel information relevant to said patient as said workflow information;

providing a centralized communication platform computer for receiving said patient information, symptoms information, patient diagnostics information, patient examination information, patient tracking location information, patient result/report information, equipment operation information, information technology medical information, rules information, and medical personnel information;

with said communication platform computer, utilizing said workflow information to automatically determine said optimized clinical workflow for said patient in advance of said patient treatment;

to automatically determine said optimized clinical workflow, said platform computer performing the steps of analyzing said workflow and further workflow information to describe and define low hanging fruits comprising easy changes with relatively high performance;

checking said information technology medical information from said at least one information technology system against said workflow information to determine interfaces and redundant data, for automating small process steps setting up an inquiry during said workflow of said tracking location information for said patient and said operation information for said at least one equipment communication unit, in a measuring and bench marking analysis determining quality measures to be used during said workflow, and determining the workflow to be followed, a kind of data needed for each step of the workflow and establishing procedures for combining and processing data from said information technology system and said patient location information; and with said centralized communication platform computer outputting the optimized clinical workflow in advance of said treatment for said patient including information for overall management of the clinical workflow and including a schedule for decision making and a check list relevant to said optimized workflow.

2. The method of claim 1 wherein said medical personnel information comprises doctor and clinical staff information.

3. The method of claim 1 wherein said workflow information further includes input to said platform computer of structured information including at least one of the elements selected from the group consisting of modalities information, doctors information, check lists information, scheduling information, suggestions information, medical reporting information, and balance scorecard information.

4. The method of claim 1 wherein said information technology information includes at least one the elements selected from the group consisting of hospital information system, radiology information system, cardiac information system, picture archiving system, and specialized information system information.

5. The method of claim 1 wherein said patient has a data card as part of said radio frequency identification tag carrying patient data which is automatically read and sent to said communication platform computer.

6. The method of claim 1 wherein said equipment comprises at least one of the elements selected from the group consisting of magnetic resonance, computer tomography and nuclear medicine equipment.

7. The method of claim 1 wherein a camera is provided for viewing at least one of the modalities magnetic resonance, computed tomography, and nuclear medicine, said camera being connected to said communication platform computer.

8. The method of claim 1 wherein said rules information comprises at least one of the elements selected from the group consisting of process descriptions, guidelines, filters, bench marks, medical knowledge, and personal doctors rules.

9. A system for automating and optimizing patient clinical workflow wherein medical personnel oversee a patient from intake through care in the clinical workflow, comprising:

said clinical workflow comprising at least the following a patient intake where patient information is provided including symptoms information as workflow information, patient diagnostics where diagnostics response information from the patient is provided to diagnostic questions to said patient as further workflow information, a patient examination where examination information for said patient is provided as further workflow information, result/report information for said patient as further workflow information, patient therapy, patient care, and patient rehabilitation, said workflow and further workflow information being obtained in advance of the patient's treatment for use in automatically determining for said patient an optimized workflow to be followed for said patient;

a patient monitoring unit in the form of a radio frequency identification tag providing tracking location information of the patient during said clinical workflow;

at least one equipment communication unit providing operation information for equipment used in the workflow in examining, treating, or caring for the patient;

at least one information technology system providing information technology medical information for said patient as said workflow information;

rules information as said workflow information;

medical personnel information relevant to said patient as said workflow information;

a centralized communication platform computer receiving said patient information, symptoms information, patient diagnostics information, patient examination information, patient tracking location information, patient result/report information, equipment operation information, information technology medical information, rules information, and medical personnel information;

said communication platform computer utilizing said workflow information to automatically determine said optimized clinical workflow for said patient in advance of said patient treatment by automatically determining said optimized clinical workflow by said platform computer performing the steps of analyzing said workflow and further workflow information to describe and define low hanging fruits comprising easy changes with relatively high performance;

checking said information technology medical information from said at least one information technology system against said workflow information to determine interfaces and redundant data, for automating small process steps setting up an inquiry during said workflow of said tracking location information for said patient and said operation information for said at least one equipment communication unit, determining in a measuring and bench marking analysis quality measures to be used during said workflow, and determining the workflow to be followed, a kind of data needed for each step of the workflow and establishing procedures for combining and processing data from said information technology system and said patient location information; and said centralized communication platform computer outputting the optimized clinical workflow in advance of said treatment for said patient including information for overall management of the clinical workflow and including a schedule for decision making and a check list relevant to said optimized workflow.

10. The system of claim 9 wherein said medical personnel information comprises doctor and clinical staff information.

11. The system of claim 9 wherein said workflow information further includes input to said platform computer of structured information including at least one of the elements selected from the group consisting of modalities information, doctors information, check lists information, scheduling information, suggestions information, medical reporting information, and balance scorecard information.

12. The system of claim 9 wherein said information technology information includes at least one the elements selected from the group consisting of hospital information system, radiology information system, cardiac information system, picture archiving system, and specialized information system information.

13. The system of claim 9 wherein said patient has a data card as part of said radio frequency identification tag carrying patient data which is automatically read and sent to said communication platform computer.

14. The system of claim 9 wherein said equipment comprises at least one of the elements selected from the group consisting of magnetic resonance, computer tomography and nuclear medicine equipment.

15. The system of claim 9 wherein a camera is provided for viewing at least one of the modalities magnetic resonance, computed tomography, and nuclear medicine, said camera being connected to said communication platform computer.

16. The system of claim 9 wherein said rules information comprises at least one of the elements selected from the group consisting of process descriptions, guidelines, filters, bench marks, medical knowledge, and personal doctors rules.

17. A computer-readable medium comprising a computer program tangibly embodied on the computer-readable medium, and when executed by a centralized communication platform computer said program automating and optimizing patient clinical workflow wherein medical personnel oversee a patient from intake through care in the clinical workflow, said clinical workflow comprising at least the following steps of obtaining patient information including symptoms information as workflow information, obtaining patient diagnostics response information from the patient to diagnostic questions to said patient as further workflow information, obtaining examination information for said patient as further workflow information, acquiring result/report information for said patient as further workflow information, providing patient therapy, providing patient care, and providing patient rehabilitation, said workflow and further workflow information being obtained in advance of the patient's treatment for use in automatically determining for said patient an optimized workflow to be followed for said patient, and wherein a patient monitoring unit is provided in the form of a radio frequency identification tag providing tracking location information of the patient during said clinical workflow, and wherein at least one equipment communication unit is provided for providing operation information for equipment used in the workflow in examining, treating, or caring for the patient, and wherein at least one information technology system is provided for providing information technology medical information for said patient as said workflow information, and wherein rules information is provided as said workflow information, as said workflow information, and wherein medical personnel information is provided relevant to said patient as said workflow information, and wherein said centralized communication platform computer receives said patient information, symptoms information, patient diagnostics information, patient examination information, patient result/report information, patient tracking location information, equipment operation information, information technology medical information, rules information, and medical personnel information, said program when executed by said platform computer performing the steps of:

utilizing said workflow information to automatically determine said optimized clinical workflow for said patient in advance of said patient treatment;

to automatically determine said optimized clinical workflow, said platform computer performing the steps of analyzing said workflow and further workflow information to describe and define low hanging fruits comprising easy changes with relatively high performance;

checking said information technology medical information from said at least one information technology system against said workflow information to determine interfaces and redundant data, for automating small process steps setting up an inquiry during said workflow of said tracking location information for said patient and said operation information for said at least one equipment communication unit, determining in a measuring and bench marking analysis quality measures to be used during said workflow, and determining the workflow to be followed, a kind of data needed for each step of the workflow and establishing procedures for combining and processing data from said information technology system and said patient location information; and outputting the optimized clinical workflow in advance of said treatment for said patient including information for overall management of the clinical workflow and including a schedule for decision making and a check list relevant to said optimized workflow.

* * * * *